United States Patent [19]

Matsuzaki et al.

[11] Patent Number: 5,162,204
[45] Date of Patent: Nov. 10, 1992

[54] APPARATUS AND METHOD OF CULTURING AND DIAGNOSIS OF ANIMAL CELLS USING IMAGE PROCESSING

[75] Inventors: Harumi Matsuzaki; Ryoichi Haga; Yuusaku Nishimura; Kenji Baba; Fumio Maruhashi, all of Hitachi; Nobuko Nishimura, Katsuta; Masahiko Ishida; Setuo Saitoh, both of Hitachi, all of Japan

[73] Assignee: Hitachi, Ltd., Tokyo, Japan

[21] Appl. No.: 347,219

[22] Filed: May 4, 1989

[30] Foreign Application Priority Data

May 6, 1988 [JP] Japan ................. 63-109028
Jul. 18, 1988 [JP] Japan ................. 63-176917

[51] Int. Cl.$^5$ .......................... C12Q 1/02; C12N 5/02; C12M 3/02; C12M 1/36
[52] U.S. Cl. ............................. 435/29; 435/240.2; 435/240.25; 435/284; 435/285; 435/286; 435/289; 435/808; 435/813
[58] Field of Search ............ 435/29, 808, 291, 240.2, 435/240.25, 289, 240.46, 813, 284, 285, 286

[56] References Cited

U.S. PATENT DOCUMENTS

| | | | |
|---|---|---|---|
| 4,661,913 | 4/1987 | Wu et al. | 436/63 |
| 4,804,628 | 2/1989 | Cracauer et al. | 435/285 X |
| 4,948,736 | 8/1990 | Kobayashi et al. | 435/813 |
| 4,957,890 | 9/1990 | Wieserman et al. | 435/176 X |

FOREIGN PATENT DOCUMENTS

| | | |
|---|---|---|
| 0336974 | 10/1989 | European Pat. Off. |
| 3139310 | 4/1983 | Fed. Rep. of Germany |
| 3516529 | 11/1985 | Fed. Rep. of Germany |
| 61-199788 | 9/1986 | Japan |

OTHER PUBLICATIONS

Wang et al. Fermentation & Enzyme Technology, John Wiley & Sons Inc, 1979, p. 100.
Cheryan and Mehaia in Membrane Separations in Biotechnology McGregor (eds), 1986, pp. 270, 285.
Patent Abstracts of Japan; & JP-A-62 201 332, (Sumitomo Electric Ind. Ltd.) dated 5 Sep. 1987.
Patent Abstracts of Japan; vol. 9, No. 153 (C-288)(1876), 27th Jun. 1985, & JP-A-60 31 888 (Hitachi Seisa Kusho K.K.) dated 18 Feb. 1985.

Primary Examiner—James C. Housel
Assistant Examiner—William Chan
Attorney, Agent, or Firm—Antonelli, Terry, Stout & Kraus

[57] ABSTRACT

An apparatus for culturing animal cells, includes a diagnosis system to make it possible to diagnose by measuring sizes of the cells by means of image processing while a system of culturing the animal cells is cut off from the outside of the apparatus system, a control system to control the culture conditions of a culturing cistern on the basis of a result of the diagnosis, and a culture medium regenerating system to remove waste contents in a culture medium. In the apparatus of this invention, the culture system and diagnosis system are cut off from the outside of the apparatus system. Therefore, no infection of miscellaneous microorganism, etc., occurs, nor does consumption of valuable cells and products occur. Further, since it is possible to easily obtain data of the proportions of division potential-possessing cells and living cells, the environmental factors to the culturing cistern can be easily and instantly controlled based on the data, and therefore, the culturing efficiency can be enhanced.

16 Claims, 7 Drawing Sheets

| $k_1$ | $k_2$ | $k_3$ |
|---|---|---|
| $k_4$ | $k_5$ | $k_6$ |
| $k_7$ | $k_8$ | $k_9$ |

FIG. 8

| m | m | m | m | m | m |
|---|---|---|---|---|---|
| m | P | P | P | P | m |
| m | P | P | P | P | m |
| m | P | P | P | P | m |
| m | P | P | P | P | m |
| m | m | m | m | m | m |

APPARATUS AND METHOD OF CULTURING AND DIAGNOSIS OF ANIMAL CELLS USING IMAGE PROCESSING

BACKGROUND OF THE INVENTION

1. Field of the Invention

This invention relates to the culturing of animal cells, and particularly it relates to an apparatus for culturing animal cells which makes it possible to measure and diagnose the activity status of animal cells under culturing while maintaining the physiological conditions of the animal cells, a culturing method and diagnostics of the culture.

2. The Related Art Statement

The production of new medical drugs by the culturing of animal cells gives as small an output as some ng-$\mu$g/$10^6$ cells.day. The improvement of the drug productivity requires (1) high densification of cells and formation of a high capacity apparatus and (2) achievement of high secretory activity of cells. In order to attain the above (2), it is necessary to measure activities of cells in a culture medium (survival, division, secretion, etc.) under the condition that the physiological conditions of the cells are maintained and the system is closed. However, under the present situation, it is general practice to determine proportions of living and dead cells according to a stain method in which a cell-staining agent is incorporated into a culture medium taken from a culturing vessel.

In the above stain method, a staining agent is incorporated, etc., i.e., the measurement cannot be made under the condition that the physiological conditions of cells are maintained, and it is therefore not possible to return the culture medium to the culturing vessel. Accordingly, the measurement system is under the open system and it is impossible to prevent infection of miscellaneous microorganisms, etc. The rate of proliferation of animal cells is as small as 1/100 of that of microorganisms. Hence, the inclusion of one microorganism in the culture system means an end of new drug production activity.

On the other hand, with regard to cells being cultured in a microscopically observable container such as a microplate, dish or culturing bottle, there is a proposal of a method by which to determine the status of cells, alive or dead, by image processing [Japanese Patent Kokai (laid-open) No. 201332/1987]. This method is applicable to species which is being cultured by using the above small containers. However, it is difficult to apply the above method to an apparatus of a practical culture scale.

Further, the above method is merely to determine the "living or dead" status of cells, and there is no industrial method to determine the activity status thereof at present.

OBJECT AND SUMMARY OF THE INVENTION

It is an object of this invention to provide a method of diagnosing the activity and culture status of cells sampled for the diagnosis, while maintaining the physiological conditions of the cells, or a method of culturing cells which makes it possible to diagnose activity status of the cells without exerting any harmful influence on the culture system, and an apparatus for working the above method.

The present inventors have investigated animal cells in a culture medium and consequently found that the size of animal cells are grouped into the following three regions.

(a) a region of only living cells (normal distribution)
(b) a region of both living and dead cells (homogeneous distribution)
(c) a region of only dead cells Accordingly, it is possible to make a diagnosis on status of animal cells, which are being cultured, by measuring the cell diameters of the animal cells.

The first aspect of this invention is directed to animal cell culturing apparatus which has a device for the above diagnosis. The embodiments thereof are as follows.

(1) An apparatus for culturing animal cells, which has a diagnosis device to make it possible to diagnose activity status of animal cells by measuring the sizes of the cells by means of image processing while maintaining their physiological conditions.

(2) An apparatus for culturing animal cells, which has, within a culture system of animal cells, a diagnosis device to make it possible to diagnose by measuring the sizes of the cells by means of image processing, and which is constituted to cut off the culture system from the outside the system.

(3) An apparatus for culturing animal cells, which has, within a vessel for culturing animal cells, a diagnosis device to make it possible to diagnose by measuring sizes of the cells by means of image processing.

(4) An apparatus for culturing animal cells, which has a system for extracting part of a cell culture medium from an animal cell culturing vessel, a diagnosing device to make it possible to diagnose by measuring sizes of the cells by means of image processing, and a system for returning measured culture cells and a medium of the cells to the culturing vessel have means to cut off themselves from the outside the individual systems.

(5) An apparatus for culturing animal cells, which has diagnosis means to make it possible to diagnose by measuring sizes of the cells by means of image processing while a system for culturing the animal cells is cut off from the outside the system, and control means to control the culture conditions of the culture vessel on the basis of the diagnostic result.

(6) An apparatus for culturing animal cells, which has a culturing vessel with control device to control environmental factors within the culturing vessel of animal cells, a diagnosis device to make it possible to diagnose the cells under culturing while maintaining physiological conditions of the cells, by measuring the sizes of the cell in a cell culture medium by means of image processing, circulation means to circulate the culture medium between the diagnosis device and the culturing vessel, and control means to control the control device of the culturing vessel on the basis of the result of image processing from the diagnosing device.

(7) An apparatus for culturing animal cells, which has diagnosing means to make it possible to diagnose by measuring sizes of the cells by means of image processing while a system for culturing the animal cells is cut off from the outside the apparatus system, control means to control the culture conditions a culturing vessel on the basis of a result of the diagnosis, and culture solution regenerating means to remove waste contents in a culture medium.

(8) An apparatus for culturing animal cells in any one of the above embodiments, which has a diagnosis device to diagnose activity status of the cells, under culturing, by measuring, by means of image processing, a distribution pattern of sizes of the cells in steady state of a culturing vessel of the cells and sizes of the cells at any cell-culturing time.

The second aspect of this invention relates to culturing method, and its embodiments are as follows.

(1) A method of culturing animal cells, which comprises taking part of a culture medium out of a culturing vessel, measuring sizes of cell particles in the culture solution by image processing while maintaining their physiological conditions, diagnosing activity status of the cells by a distribution of the sizes of the cell, and controlling the culture conditions of the culturing vessel on the basis of the diagnostic result.

(2) A method of culturing animal cells, which comprises, while a culture system is cut off from the outside the system, taking part of a culture medium out of a culturing vessel measuring sizes of cell in the culture medium by image processing, diagnosing activity status of the cells by a distribution of the sizes of the cell, and controlling the culture conditions of the culturing vessel on the basis of the diagnostic result.

(3) A method of culturing animal cells in any of the above embodiments (1) and (2), in which the culture solution used for the above diagnosis is cultured while recovering same into the culturing vessel.

The third aspect of this invention relates to diagnostics, and its embodiments are as follows.

(1) A method of diagnosing animal cells which comprises preliminarily diagnosing sizes of living cells and dead cells from a distribution pattern of sizes of cell in a culturing vessel of the animal cells in steady state, and measuring a distribution of the sizes of the cell at any culturing time by means of image processing and by using the above diagnostic result as a standard, thereby to diagnose activity status of animal cells.

(2) A method of diagnosing animal cells which comprises taking part of a culture medium out of a culturing vessel, changing a cells-suspending culture medium, which has been introduced into an observation portion cell while maintaining their physilogical conditions, to image signals by image taking means, converting the analog signals of the image into digital signals by image processing means, storing brightnesses of pixels of the image in image memory means as a multi-value image data, calculating the stored multi-value image data by cell image recognizition means for a particle size distribution of all of the cells whose images are taken, and comparing the resultant distribution with the size distribution of the cells in culture steady state, thereby to diagnose activity status of the cells.

(3) A device for diagnosing animal cells, which has connection means to connect to a culturing vessel of the animal cells and means of measuring sizes of cell particles in a cell culture medium taken out of the culturing vessel through the above connecting means, by means of image processing while maintaining physiological conditions.

This invention can be applied to culturing animal cell strains such as human lymphoblast (IM-9: U.S. A.T.C.C.), rat liver cell JTC-1, mouse-mouse hybridoma (STK-1: U.S. A.T.C.C.), etc.

Figure 1:
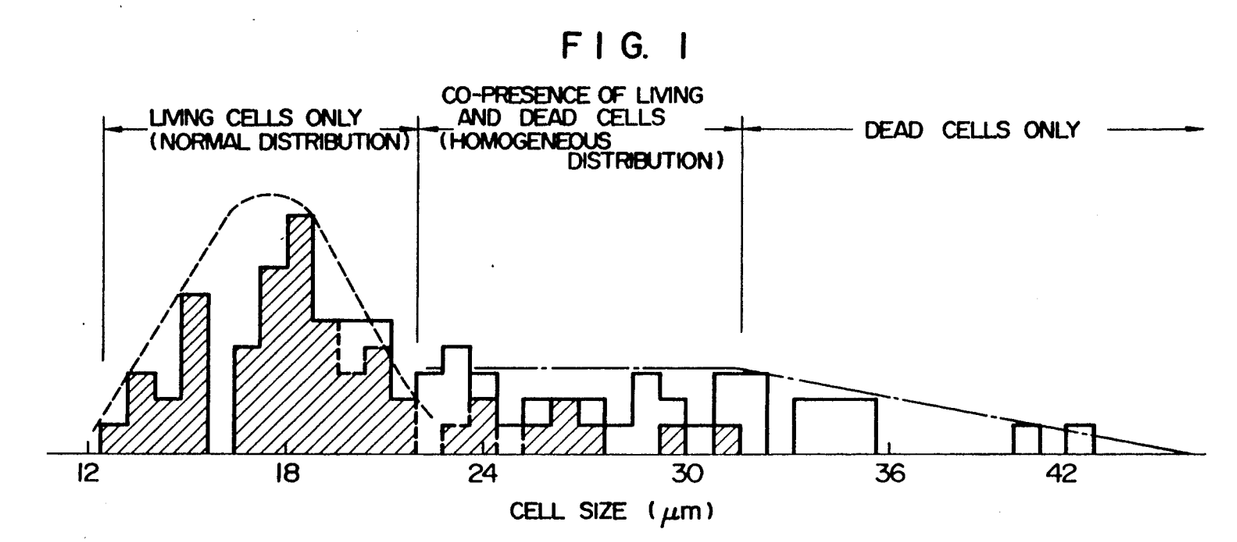
FIG. 1 shows experimental data for sizes and distribution states of animal cells.

Needless to say that this invention is applicable to culturing of any cells that exhibit a cell size distribution as shown in FIG. 1 which will be discussed later.

DETAILED DESCRIPTION OF THE PREFERRED EMBODIMENTS

According to FIG. 1, the judgement on the "living or dead" state of cells will be explained.

FIG. 1 shows one example of cell size distributions obtained by microscopic observation of about 100 cells fixed by the stain method from rat liver cells JTC-1 in a steady state during a culturing process. In the Figure, that portion of the distribution which is indicated by hatching shows living cells, and that portion of the distribution which is indicated by void shows dead cells. The sizes of cells are distributed in the range from 10 μm and some to 40 μm and some. And the living cells are distributed on the smaller-number side and dead cells are distributed on the larger-number side. The above distribution consists of ① a region of only living cells,
② a region of both living and dead cells, and
③ a region of only dead cells.

On the basis of the above characteristic constitution of distribution, it is possible to determine proportions of living cells, dead cells and division potential-possessing cells. The living cells/dead cells ratio in the above region of both living and dead cells is 1:1, and the living cells in the region of both living and dead cells do not have any division potential. The living cells distributed in the above region ① have division potential.

Figure 2:
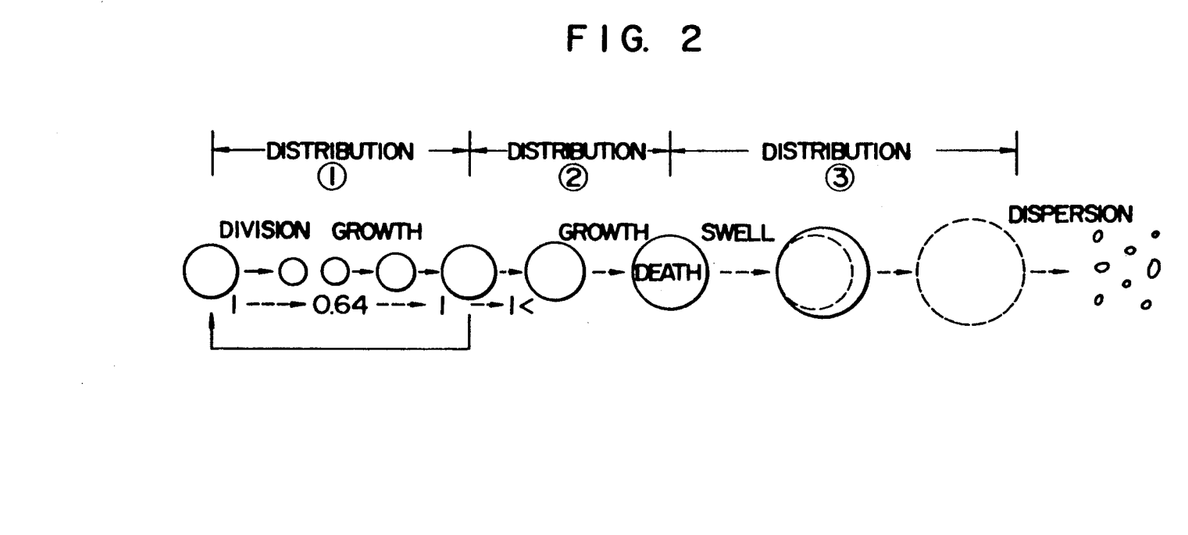
FIG. 2 shows a model for states of growth, division and death of animal cells.

The above distribution of cell sizes is in agreement with progressive phenomena of growth, division and death of cells typically shown in FIG. 2. Statistically, when a cell grows to a certain size (two-dimensional size: its area is taken as 1), the cell undergoes division, and physically, its area after the division is 0.64 of the area which the cell had before the division. When reproduced cells grow to a size having an area of 1, the cells undergo division. The areas of division potential-possessing cells range between 0.64 and 1. A cell, which does not undergo division any longer, further grows over the area of 1 until its final death.

After a cell dies, cytoplasms such as mitochondoria, etc., flow out of the cell, and the cell swells to increase its size apparently. Its nucleus disappears and finally the cell is dispersed in a culture medium. In correspondence between the course of growth, division and death and the distribution of cell sizes shown in FIG. 1, the state of area of 1 corresponds to a boundary between the distributions ① and ②, and the state of final death of the cell corresponds to a boundary between the distributions ② and ③. An actual course of cell culturing shows variations in the sizes of cells which finally die, and therefore the distribution ② appears. In the living cells/dead cells ratio in the distribution ②, the smaller the cell sizes are, the larger the proportion of living cells is, and the larger the cell sizes are, the smaller the proportion of living cells is. The living cells/dead cells ratio in the distribution ② is nearly 1:1.

As mentioned above, it is possible to determine the living/dead ratio and division activities of cells by measuring cell size distributions. The measurement of cell size distributions can be carried out without incorporating any foreign substance into a culture system. Therefore, the above activities of cells can be diagnosed without isolating the cells from their culture system.

EXAMPLES

Figure 3:
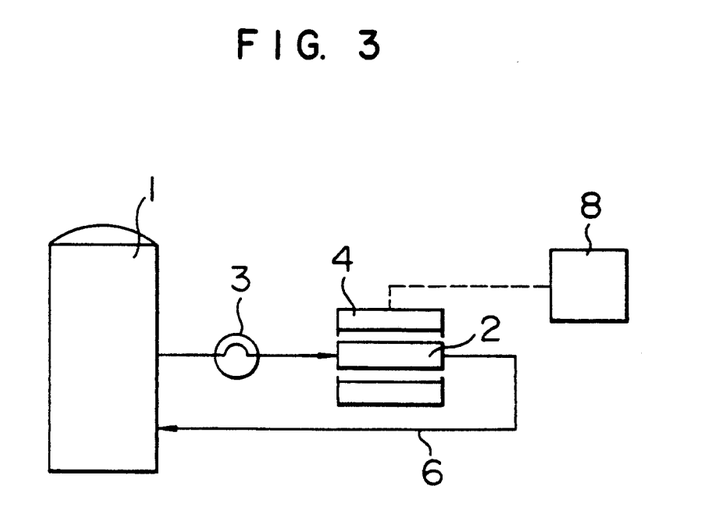
FIGS. 3 to 5 are schematic views showing a device for diagnosing cell activity in this invention.

FIG. 3 shows a device for diagnosing cells as one embodiment of this invention. The apparatus comprises a culturing vessel 1, a culture medium observing portion 2, means 3 of introducing a culture medium to the observing portion 2, a measuring device 4 to measure sizes of cells in the observing portion 2, an analyzer 8 to determine a proportion of division potential-possessing cells (or proportion of division potential-not possessing cells) or a proportion of living cells (or proportion of dead cells) on the basis of a cell size distribution, and means 6 to return a culture medium in the observing portion 2 to a culture medium in the culturing vessel. The means 3 and 6 and the observing portion 2 are constituted such that the culture medium can be recycled under a condition of its isolation from the outside the culture system.

The culture medium in the culturing vessel is partially fed to the observing portion 2, and cells in the partially fed culture medium in the observing portion 2 are measured by the measuring device 4 for a cell size distribution. An equivalent diameter or area may be used to represent the cell size. When the measurement is finished, the culture medium in the observing portion 2 is returned into the culturing vessel 1. An information on the cell size is transmitted from the measuring device 4 to the analyzer 8, and the analyzer 8 determines activity of cells (division activity, life-maintenance activity) on the basis of the above information to display the result.

In general, the culture medium is intermittently fed from the culturing vessel 1 to the measuring portion 2. However, there are some types of measuring devices which can measure the above distribution while the culture medium is fed continuously.

Figure 4:
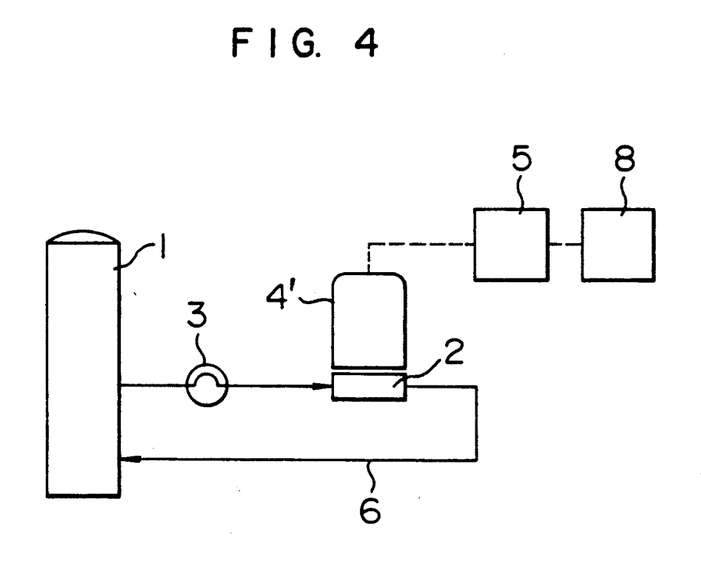

FIG. 4 shows a device for diagnosing cell activity as one embodiment of this invention, in which an image processing device is used in the above measuring device 4. The image processing device comprises an image taking means 4' and an image processing means 5. An image of cells is transmitted from the image taking means 4' to the image processing means 5. Preferably, the image taking means 4' has a magnifying function such as a microscopic function. The flow rate of a culture medium in the observing portion 2 may be about a rate of precipitation of cells in a stationary culture medium.

Figure 5:
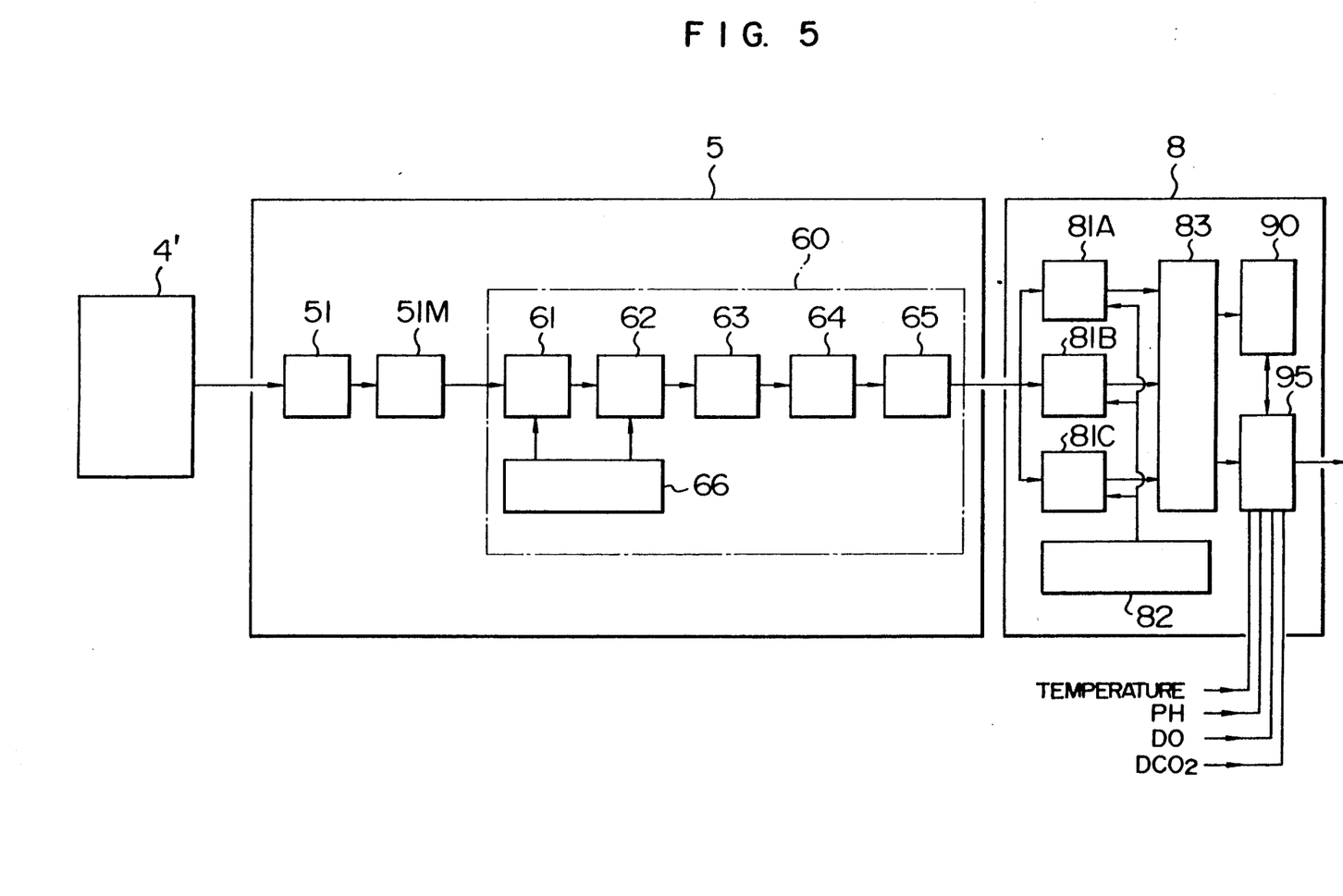

FIG. 5 shows detailed constitutions of the image processing device 5 and the analyzer 8, and their actions will be explained hereinbelow.

At first, image signals obtained by the image taking device 4' are transmitted to an A/D converter 51 of the image processing device 5. The A/D converter 51 converts analog signals of an image to digital signals. That is, the image is not only divided vertically and horizontally into small pixels, but also A/D converted image signals are formed into a multi-element image in which the pixels have digital brightness values. For example, an image is divided vertically and horizontally into 256 by 256 pixels and digitized with resolution of 128-step brightnesses. The A/D converted image signals are stored in an image memory 51M. The multi-element image stored in the image memory 51M is transmitted to a cell image recognition circuit 60. The cell image recognition circuit 60 recognizes all of the cells regardless of their life or death, calculates their number and sizes, and calculates their particle diameter distribution. The calculation results are transmitted to the analyzer 8, and the analyzer calculates, on the basis of the above calculation results, the numbers of living cells and dead cells and the number of division potential-possessing cells, and at the same time diagnoses activity status of the grouped cells on the basis of these calculation results.

Figure 6:
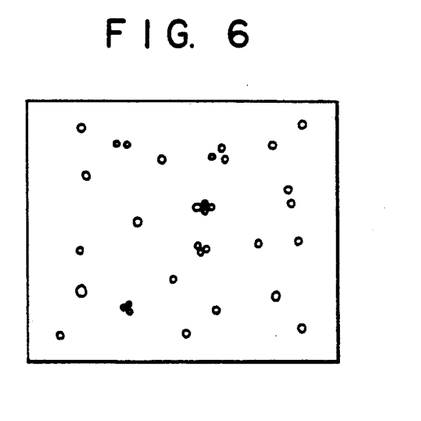
FIGS. 6 and 7 are schematic views showing the diagnosis of cell activity and control system of culturing cistern in this invention.

FIG. 6 shows an embodiment of multi-value image data stored in the image memory 51M. The multi-element image stands for an image of which the pixels are different in the brightness, as explained previously. Some cells have large sizes and the other cells have small sizes. In FIG. 6, cells having small particle diameters represent living cells, and cells having large particle diameters represent dead cells. Cells having diameters in between represent those in the state in which living cells and dead ones are co-present. The image in FIG. 6 is transmitted to the cell image recognition circuit 60, which recognizes all of the cells regardless of their life or death, and calculates the number, size, form and brightness of the cells, etc. This Example will explain a calculation of the size and number.

Figure 7:
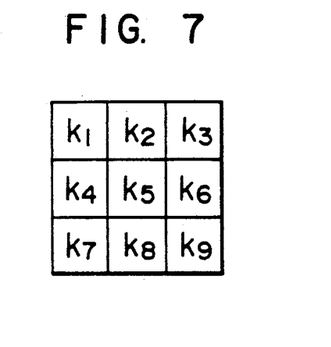

A pre-processing circuit 61 effects the pre-processing in order to recognize the cells from the multi-element image of the image memory 51M. Examples of the pre-processing include smoothing, brightness emphasis, outline emphasis, etc. However, in order to recognize cells, mere spatial filtering treatment is not sufficient in accuracy, and particularly, brightness emphasizing treatment before the spatial filtering treatment is effective. The maximum brightness emphasizing treatment is one type of nonlinear neibourhood calculation, and its specific details will be explained according to FIG. 7. In a region of 3×3 pixels (of which the brightnesses are indicated by $k_1$ to $k_9$) having a pixels of brightness $k_5$ in the middle as shown in FIG. 7, the maximum brightness in the region is newly substituted in the picture element of brightness $k_5$. The calculation formula is as follows.

$$k_8 = \text{MAX}\,[k_1 \sim k_9] \quad (1)$$

For example, if $k_1$ is the highest brightness among $k_1$ to $k_9$, i.e., MAX $[k_1 \sim k_9] = k_1$, then the brightness of the pixel having a brightness $k_5$ is changed to $k_1$. All the picture elements are treated in the same way as mentioned here to obtain a new multi-value image data. This treatment has a function to emphasize the brightness of the central portion of a cell since the central portion has high brightness.

Figure 8:
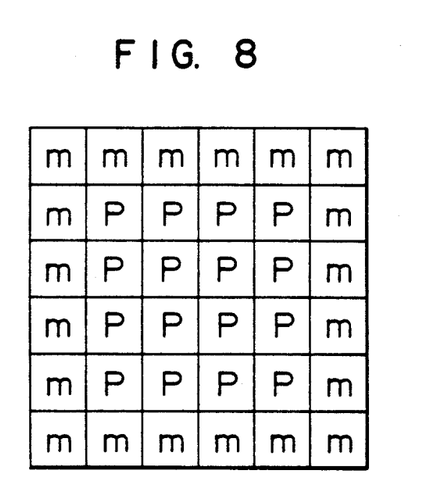
FIGS. 8 to 9 show typical views for a method of processing images of cells which are being cultured.

Further, there is also a function to erase dark portions of a cell outline. In addition, in the pre-processing circuit 61, it is further effective to carry out spatial filtering treatment in order to emphasize bright portions by using a mask pattern shown in FIG. 8. In FIG. 8, p's represent positive values, and m's represent negative values. This treatment makes it possible to selectively emphasize cells alone.

Figure 9:
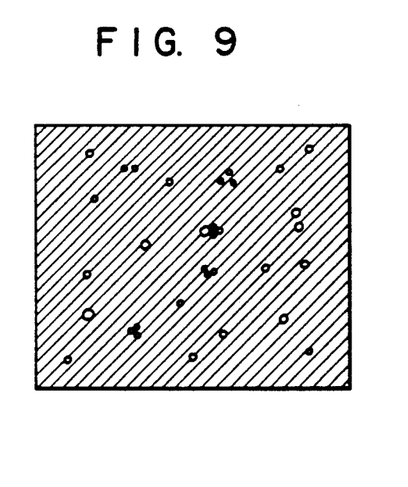

A binalization circuit 62 achieves binalization in which portions having higher brightnesses than the given brightness $k_a$ are set as "1" and the other portions as "0". FIG. 9 shows an image obtained by this binalization of the image of FIG. 6. In FIG. 9, portions indicated by slanting lines show background, and void portions show cells. If cells are large and interiors of the cells are binalized as blank, blank-filling treatment is carried out, although its explanation is omitted here. By the above procedures, it is possible to selectively recognize cells alone. The parameters, m, p, $k_a$, etc., which are necessary for the preprocessing and binalization, are set by a conditioning circuit 66.

With regard to an image binalized by the binalization circuit 62, a labeling circuit 63 labels numbers on cells therein and counts their numbers, and every cell is subjected to the following treatment. That is, a next area calculation circuit 64 calculates an area of every cell. Then, a circuit 5, for calculation of a cell diameter distribution, calculates a diameter by classifying areas of the cells. For example, the classification is effected every 1 μm. In this case, a circle-equivalent diameter, etc., may be used as a typical cell diameter. The calculated cell diameter distribution is transmitted to the analyzer 8.

Figure 10:
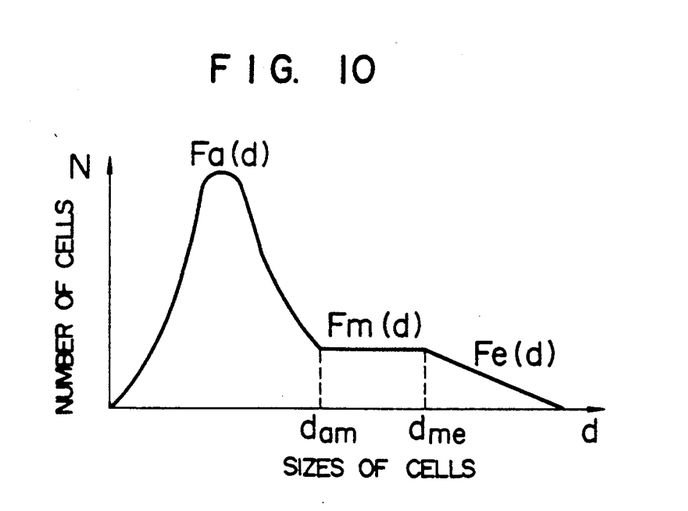
FIG. 10 shows an example of the resultant cell diameter distribution.

The analyzer 8 receives values of the cell size distribution and diagnoses activities of the cell groups totally. An example of the resultant cell diameter distribution is shown in FIG. 10. This principle is accomplished by forming a model of a relationship between growth of cells (increase in cell diameter) and their diameter distribution. That is, in the analyzer 8, a living cell calculation circuit 81A, a dead cell calculation circuit 81B and a co-present cell calculation circuit 81C calculate numbers of grouped cells, respectively. In other words, a formula of living cells (2), formula of dead cells (3) and formula of living and dead cells co-present state (4) are formed into models with separate distributions of each diameters. Namely, provided that cell diameters present in boundaries of the grouped cells are $d_{am}$ and $d_{me}$ as shown in FIG. 10:

living cell $d \leq d_{am}$ : $N(d_a) = F_a(d)$ (2)

dead cell $d > d_{me}$ : $N(d_e) = F_e(d)$ (3)

co-presence $d_{am} < d \leq d_{me}$ : $N(d_m) = F_m(d)$ (4)

total number of cells : $N_t(d) = N(d_a) + N(d_e) + N(d_m)$ (5)

In the above formulae, $d_a$, $d_e$ and $d_m$ represent cell diameters of living cells only, dead cells only and living and dead cells co-present state, respectively, and $N(d_a)$, $N(d_e)$ and $N(d_m)$ represent numbers of such cells, respectively. Further, $F_a(d)$, $F_e(d)$ and $F_m(d)$ are functions of cell diameter distributions, and $F_a(d)$ is a normal distribution, $F_m(d)$ is a homogeneous distribution and $F_e(d)$ is a monotone decrease type distribution (e.g., exponential distribution). As mentioned here, the living cell calculation circuit 81A, dead cell calculation circuit 81B and co-present cell calculation circuit 81C carry out calculations to apply models-forming particle diameter distributions to the cell particle diameter distribution transmitted from the cell image recognition circuit 60, thereby to determine the cell diameters $d_{am}$ and $d_{me}$ which are boundaries of the individual distributions. If the boundary cell diameters $d_{am}$ and $d_{me}$ are determined, $N(d_a)$, $N(d_e)$ and $N(d_m)$ can be easily obtained from the cell diameter distribution transmitted from the cell image recognition circuit 60. The above $N(d_a)$, $N(d_e)$ and $N(d_m)$ can also be obtained by inputting $d_{am}$ and $d_{me}$ through the conditioning circuit 82 in the steady state.

The number of cells in each of the distributions can be calculated as mentioned above. Therefore, various activities of the cell groups as a whole can be diagnosed. Diagnostics will be discussed concretely hereinbelow.

An activity calculation circuit 83 calculates, for example, a cell survival rate $\epsilon$ in the following formula.

$$\epsilon = \frac{N(d_a) + \frac{1}{2}(d_m)}{N_t(d)} \quad (6)$$

In the activity calculation circuit 83, a division portential-possessing cell ratio $\eta$ is calculated in the following formula.

$$\eta = \frac{N(d_a)}{N(d_a) + \frac{1}{2} N(d_m)} \quad (7)$$

Similarly, in the activity calculation circuit 83, a dead cell ratio $R_e$ is calculated in the following formula.

$$R_e = \frac{N(d_e) + \frac{1}{2} N(d_m)}{N_t(d)} \quad (8)$$

In addition to the above, in the activity calculation circuit 83, temporal changes of living cells $\{N(d_a) + \frac{1}{2} N(d_m)\}$ and dead cells $\{N(d_e) + \frac{1}{2} N(d_m)\}$ are calculated, i.e., a rate of proliferation and a rate of death are calculated in the following formulae.

$$\text{Rate of proliferation} = \frac{d\left(N(d_a) + \frac{1}{2} N(d_m)\right)}{dt} \quad (9)$$

$$\text{Rate of death} = \frac{d\left(N(d_e) + \frac{1}{2} N(d_m)\right)}{dt} \quad (10)$$

On the basis of these formulae, cells are diagnosed for proliferation, activity decrease or death state. For example, even if $R_e$ is large, the higher rate of proliferation indicates the higher proliferation potency and activity of the cells. Even if $R_e$ is small, the higher rate of death indicates not only rapid death of the cells but also low activity of the cells. The activities of cell groups are diagnosed as mentioned above.

These diagnostic results are inputted to an inference engine 95. Also inputted to the inference engine 95 are values measured by a temperature sensor, a pH sensor, dissolved oxygen (DO) sensor and a dissolved carbon dioxide gas ($DCO_2$) sensor as cell culture environmental factors. On the other hand, assorted experimental and theoretical data of proliferation and metabolism of cells are stored in a data base 90. The inference engine 95 infers status of cells on the basis of information of the data base, measured values of culture environment and diagnostic results of image-measurement of cell groups, and inputs a command to a computer as necessary in order to control the culture environment. For example, when DO decreases to lower the proliferation rate of cells, the inference engine 95 infers DO shortage and increases the rate of bubble generation by a compressor to increase DO. When pH lowers to increase the rate of death, the inference engine 95 infers that pH is too low, and increases pH by feeding an alkali agent, adjusting the partial pressure of carbon dioxide gas, or the like.

Figure 11:
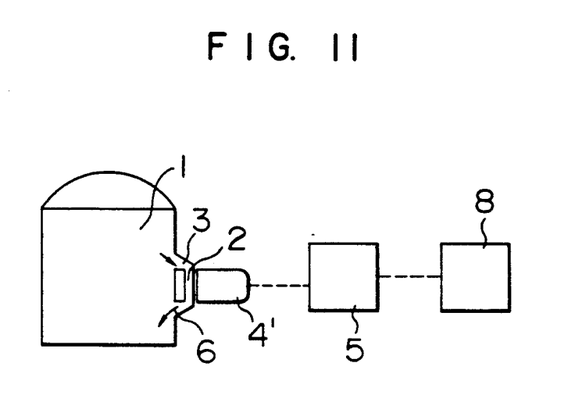
FIG. 11 shows an apparatus for diagnosing cell activity as one embodiment of this invention.

FIG. 11 shows an apparatus for diagnosing cell activity as one embodiment of this invention. This apparatus is an integral constitution of the culturing vessel 1 and observing portion 2 shown in FIG. 4, in which a culture medium in the culturing vessel is partially fed to the observing portion 2 by a spinner flow in the culturing vessel and the culture medium is returned from the observing portion 2 into the culturing vessel.

Figure 12:
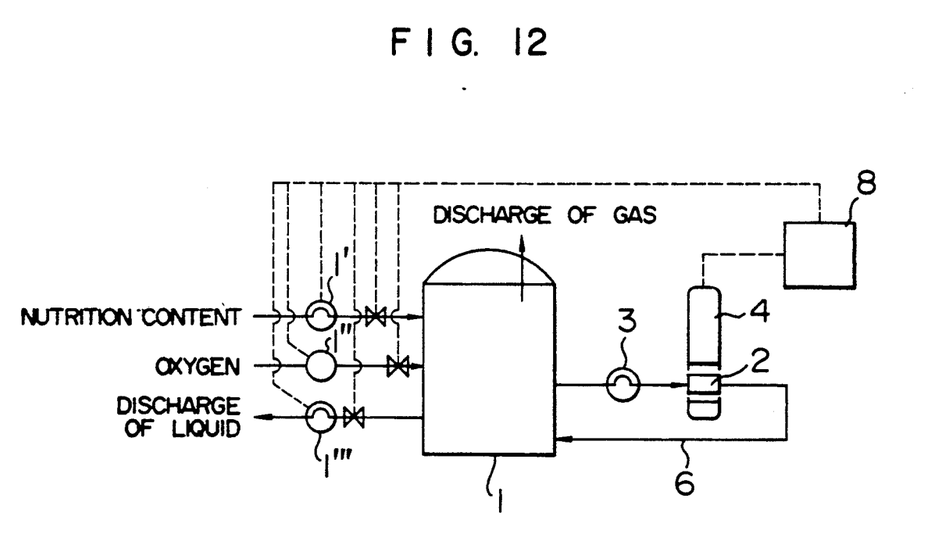
FIG. 12 shows a device for controlling diagnosis of cell activity as one embodiment of this invention.

FIG. 12 shows a device for controlling diagnosis of cell activity as one embodiment of this invention. This apparatus comprises a culturing vessel 1 having means (1', 1'', 1''', etc.) of adjusting environmental factors to a culture medium within the culturing vessel (nutrition contents concentration, dissolved oxygen concentration, concentration of waste products such as ammonia, lactic acid or the like, ages of cells, product concentration, etc.), an observing portion 2, an introduction device 3 to introduce a culture medium to the observing portion 2, a measuring device 4 to measure a distribution of cell sizes in the observing portion 2, an analyzer 8 to determine, from the cell size distribution, a proportion of division potential-possessing cells (or proportion of division potential-not possessing cells) or a proportion of living cells (or proportion of dead cells), and means 6 of returning the culture medium in the observing portion 2 into the culture medium within the culturing vessel. The above means 3 and 6 and the observing portion 2 are constituted such that the culture medium is recycled under the condition that it is cut off from the outside the culture system.

The culture medium in the culturing vessel is partially fed to the observing portion 2, and cells in the fed culture medium are measured by the measuring device 4 for a distribution of their sizes. Nominal diameters, areas, etc., may be used to represent sizes of the cells. The culture medium used for measurement in the observing portion 2 is returned into the culturing vessel 1. An information of a cell size distribution is transmitted from the measuring device 4 to the analyzer 8, which determines cell activities (division activity, survival activity) on the basis of the above information. Further, the analyzer 8 properly adjusts the environmental conditions to the culture medium in the culturing vessel by controlling the above adjusting means 1', 1'', 1''', etc., on the basis of the resultant cell activities.

The method of controlling the environmental conditions to the culture medium in the culturing vessel will be explained hereinbelow.

By using a proportion 0 of division potential-possessing cells (=number of division potential-possessing cells/number of living cells) and a proportion $\epsilon$ of living cells (=number of living cells/number of total cells), the number N of living cells to be found in t hours' time can be represented by the following formula.

$$N = \frac{1}{2} N_0 \left( \frac{1 - (2\eta)^{\frac{t}{T}+1}}{1 - (2\eta)} + 1 \right) \quad (11)$$

wherein if $(n+1)T > t \geq nT$, then $t/T = n$

In the above formula, $N_O$ represents a total cell number when $t=0$ and T is a cell cycle, and n is 0 or a positive integer.

That is, it is possible to simulate the number of living cells in t hours' time by using formula (11). On the basis of the result of the above simulation, it is also possible to control the environmental conditions to the culture medium in the culturing vessel. In addition to the disolved oxygen concentration, nutrition contents concentration and waste contents concentration in the culture medium, the above environmental conditions include the following values P and Q.

$$P = \text{cell concentration} \times \text{stay time} \quad (12)$$

$$Q = \frac{\text{cell concentration} \times \text{stay time}}{\text{buoyant substance concentration in fed nutrition content liquid}} \quad (13)$$

By controlling the above value P or Q such that it is in a given range while considering the above environmental conditions, it is possible to control various activities of cells (respiratory activity, proliferation activity, secretory activity, endogenous respiratory activity, etc.). That is, it is possible to control activities optionally; for example, the proliferation activity can be enhanced more than the other activities, the secretory activity can be enhanced more than the other activities, and the like.

The following is an explanation of a measuring device cell to measure the cell sizes in this invention.

Figure 13:
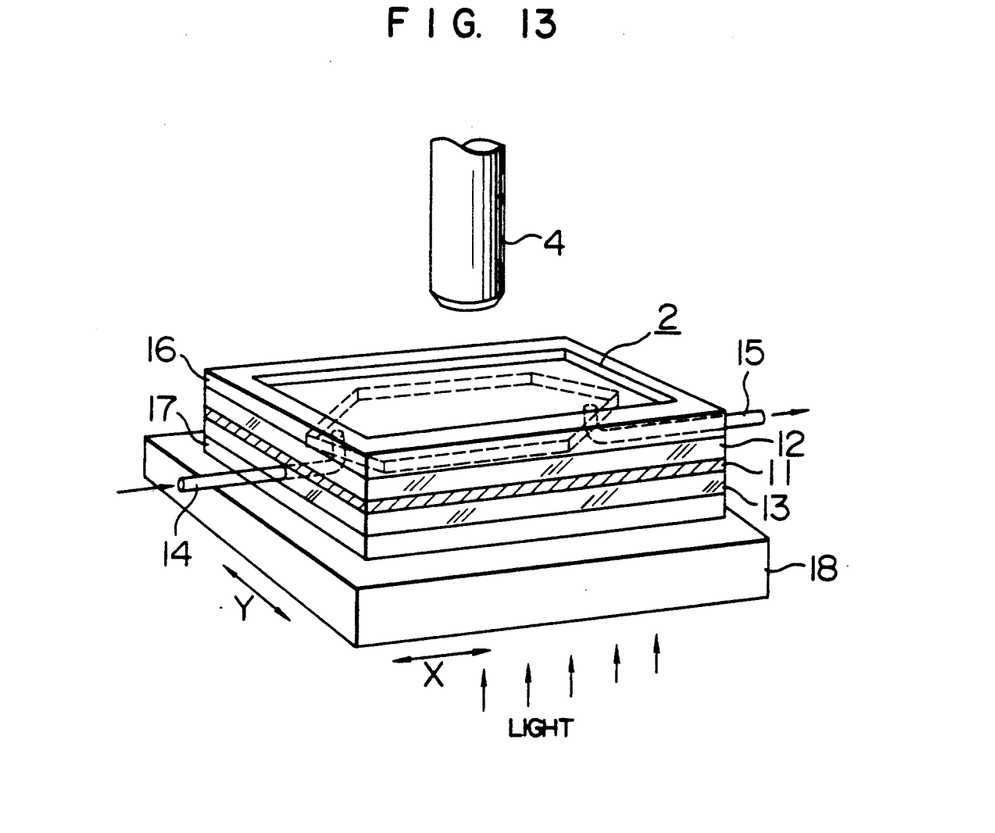
FIGS. 13 and 14 schematically show perspective views of a cell for diagnosing cells as one embodiment of this invention.
Figure 14:
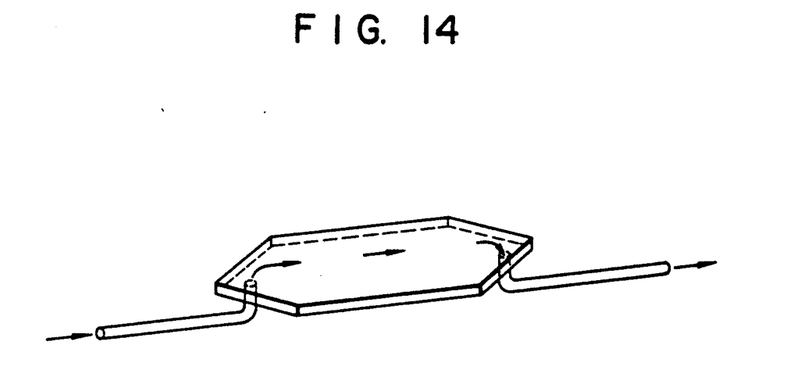

FIG. 13 is a perspective view showing one embodiment of said cell. FIG. 14 is a typical perspective view of a cell portion in which a culture medium of cells flows.

The observing portion cell 2 has a cell structure as shown in FIG. 14, which is formed by using, as a spacer 11, a film of polytetraethylene (having a thickness of about 100 μm( with a hexagonal window, and placing the film between two glass sheets 12 and 13. The two glass sheets are fastened by two metal supporter frames 16 and 17 and screws (not shown). The cell is provided with an inflow tube 14 of a cell culture medium and an outflow tube 15 thereof. In addition, the observing portion cell can be subjected to sterilization treatment under heat (120° C.).

Further, the above cell is placed on a stage 18 which is movable freely in the direction of X—Y, and is provided with a constitution which makes it possible to make observation through the measuring device 4 placed above the cell and by light emitted from a light source (not shown) placed in the lower portion of the stage.

A culture medium is introduced into the cell by the inflow tube 14 from a circulation pipe (not shown) connected to the culturing vessel, and the stage and an observing device are manipulated to observe sizes of animal cells. In diagnosis of the activity status of cells, an image of cells, which is taken by a image making device (indicated a 4' in FIG. 4) attached to the measuring device 4, is processed by an image processing means (indicated as 5 in FIG. 4), and the resultant data id diagnosed by an analyzing means (indicated as 8 in FIG. 4).

The culture medium containing the measured cells is returned to the culturing vessel through the outflow tube 15.

As mentioned above, since this embodiment makes it possible to diagnose the activity status of cells in the state wherein the culture system and diagnosis system are cut off from the outside the apparatus system, there is not any risk of miscellaneous microorganisms infection, nor is there any loss of products such as a culture medium, etc.

As discussed hereinabove, in this invention, the culture system and diagnosis system are cut off or isolated from the outside the apparatus system. Therefore, there is no infection of miscellaneous microorganisms, etc., and valuable cells and products are not consumed. Further, since it is possible to easily obtain data of the proportion of division potential-possessing cells and the proportion of living cells, it is easily and instantly control the environmental factors to the culturing vessel on the basis of the data. Therefore, the culturing efficiency can be enhanced.

One embodiment of the animal cell culture system, which is precedent to the foregoing diagnosis of animal cell activities, will be explained hereinbelow.

Figure 15:
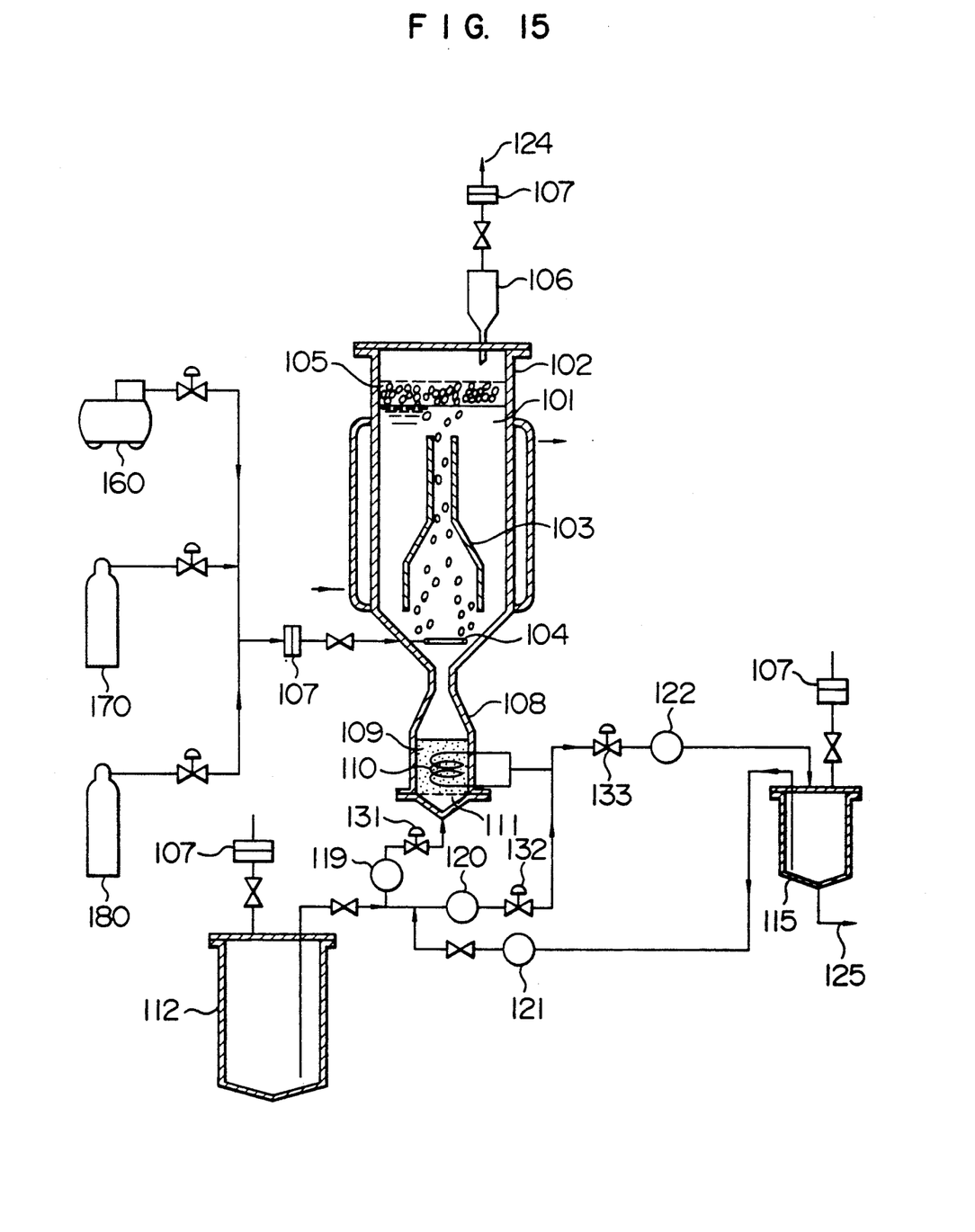
FIG. 15 shows a constitution of a system for culturing animal cells.

FIG. 15 shows a constitution of one embodiment of a cell culture system usable in this invention.

In a culturing vessel 102, cells are cultured by being dispersed and suspended in a culture medium 101. The culturing vessel is provided, in its bottom portion, with a nozzle to aerate the medium with an oxygen-containing gas, through which oxygen necessary for growth of cells and carbon dioxide gas necessary for pH adjustment are fed. That is, air from an air compressor 160 and an oxygen-containing gas from a container 170 are flow-controlled such that the dissolved oxygen concentration is constant, and further a carbon dioxide gas from a container 180 is flow-controlled such that the pH is between 7.0 and 7.6. These gases are passed through a sterilizing filter 107 and then blown in through the nozzle 104. The gas blown into the solution starts the culture medium flowing by forming bubbles and ascending toward the surface of the medium. A draft tube 103 is provided in order to achieve the effective flow of the culture medium started by the blown gas. Bubbles having reached the medium surface form a bubble layer without breakage, and they are therefore broken effectively by bringing them into contact with a antifoaming agent layer 105 formed of a water repellent material above the medium surface.

Gas is discharged, as discharge gas 124, out of the culturing vessel through a mist separator 106 and a filter 107. In addition, the culturing vessel 102 is provided with various devices such as means of introducing culture medium to the observing portion, means of adjusting a dissolved gas concentration and pH to constant levels, means of sterilizing the interiors of the vessel and tubes, means of charging and discharging culture medium, means of maintaining temperature at a given level, sensors to detect a dissolved oxygen concentration, pH, temperature, internal pressure of the vessel, medium surface level of the vessel, etc., and the like. However, these devices are not shown in FIG. 15.

The culturing vessel 102 is provided with a filtration device 108 in its lower portion. The filtration device 108 is provided with a porous hollow fiber membrane filter 110 inside and with a filter auxiliary 109 on or around the filter. The filter auxiliary 109 is supported by a support filter 111.

It is to be noted that the hollow fiber membrane filter 110 changes its form or exposes itself from the layer of the filter auxiliary 109 when the solution moves rapidly at the time of sterilization, backwash, etc. However, its form is not specially limited.

The culture solution exchange is carried out as follows. In FIG. 15, valves 131 and 132 are closed, a valve 133 is opened and a pump 122 is actuated to introduce a culture medium 101 from the culturing vessel 102 to the filtration device 108. Cells in the culture medium are collected on the surfaces of the filter auxiliary 109 and porous hollow fiber membrane filter 110 when the culture solution passes therethrough. The porous hollow fiber membrane filter 110 is selected such that it has an opening degree of preventing the passage of cells of the filter auxiliary 109 and the cells. A filtrate of the culture medium, from which the cells are filtered, is stored in a culture medium storage tank 115.

After a given amount of the culture medium is discharged from the culturing vessel 102, the pump 122 is stopped and the valve 133 is closed. Then, the valves 131 and 132 are opened, and pumps 119 and 120 are actuated. The pumps 119 and 120 feed a fresh culture medium from a fresh culture medium storage tank 112 to the filtration device. In this case, the pump 119 feeds the fresh culture medium from the bottom portion of the filtration device 108, and its feed rate is set so as to float and spread the filter layer of the filter auxiliary 109. The pump 120 reversely charges a fresh culture medium under pressure onto the porous hollow fiber membrane filter 110 for its backwash, thereby to separate solid substances such as cells, etc., from the surface of the filter 110. In addition, the flow rates of the pumps 119 and 120 are adjusted so as not to cause dissipation of the filter auxiliary 109 from around the filtration device.

The cells collected on the filtration auxiliary 109 and the hollow fiber membrane filter 110 in the above filtration step were released out of the filler layer by the spreading of the filtration auxiliary 109. The specific gravity, size and form of the particles of the filtration auxiliary 109 are selected such that the settling rate of the particles is higher than that of the cells. Therefore, the cells are floated up to the upper portion of the spreaded filler layer, and back to the culturing vessel 102 together with the fresh culture medium. In addition, numeral 121 indicates a pump and numeral 125 indicates a tubing system from the culture filtrate tank.

We claim:

1. A method of culturing animal cells, which comprises the steps of:
   taking part of a culture liquid containing the animal cells out of a culturing vessel which is isolated from ambient environment;
   taking an optical image of the part of the culture liquid through an optical device;
   converting the optical image into electrical signals;
   measuring sizes of animal cells in the culture liquid by image processing based on the electric signals;
   calculating a cell size distribution of the animal cells based on the measured cell sizes;
   diagnosing activity status of the animal cells from the distribution; and returning the taken part of the culture liquid to the culturing vessel, wherein the taken part of the culture liquid is isolated from the ambient environment and the same physiological conditions of the taken part of the culture liquid as in the culturing vessel is maintained while the taken part of the culture liquid is out of the culturing vessel.

2. The method according to claim 1, wherein the cell size distribution is divided into three portions, first one of which is normal distribution as a living cell region, second one is a homogeneous distribution as a co-presence of living cell and dead cell region, and third one is a dead cell region.

3. A method of culturing animal cells, which comprises the steps of:

taking part of a culture liquid containing the animal cells out of a culturing vessel which is isolated from ambient environment;

taking an image of the part of the culture liquid through an optical device;

converting the image into an electric signal;

measuring sizes of animal cells in the part of the culture liquid by image processing based on the electric signal;

calculating a cell size distribution of the animal cells in the taken part of the culture liquid based on the electric signal;

diagnosing activity status of the animal cells from the calculated distribution of the sizes of the cells; and returning the part of the culture liquid to the culturing vessel, wherein the culture liquid is isolated from the ambient environment and the same physiological conditions of the taken part of the culture liquid as in the culturing vessel is maintained throughout the step of culturing.

4. The method according to claim 3, wherein the cell size distribution is divided into three portions, first one of which is a normal distribution as a living cell region, second one is a homogeneous distribution as a co-presence of living cell and dead cell region, and third one is a dead cell region.

5. A method of culturing animal cells, which comprises the steps of:

taking part of a culture liquid out of a culturing vessel which is isolated from ambient environment;

taking images of the cells in the part of the culture liquid by means of an optical device;

converting the images into electric signals;

measuring sizes of animal cells in the part of the culture liquid by image processing;

calculating a cell size distribution based on the electric signals;

wherein the taken part of the culture liquid is isolated from the ambient environment and the physiological conditions of the taken part of the culture liquid is maintained in the same condition as in the culturing vessel, until the taken part of the culture liquid is returned to the culturing vessel;

diagnosing activity status of the animal cells based on the calculated size distribution of the animal cells;

returning the taken part of the culture liquid to the culturing vessel; and controlling the culture conditions of the culturing vessel on the basis of a control signal based on the cell size distribution of the animal cells.

6. The method according to claim 5, wherein the cell size distribution is divided into three portions, first one of which is a normal distribution as a living cell region, second one is a homogeneous distribution as a co-presence of living cell and dead cell region, and third one is a dead cell region.

7. A method of culturing animal cells, which comprises the steps of:

taking part of a culture liquid out of a culturing vessel which is isolated from ambient environment;

taking images of the cells in the part of the culture liquid by means of an optical device;

measuring sizes of animal cells in part of the culture liquid by image processing while maintaining the physiological conditions of the taken part of the culture liquid the same as in the culturing vessel;

calculating a cell size distribution based on the measured cell size;

diagnosing activity status of the animal cells from the cell size distribution;

controlling the culture conditions of the culturing vessel based on a control signal derived from the measured sizes of the animal cells; and returning the taken part of the culture liquid containing the animal cells to the culturing vessel, while avoiding any contaminates from entering into the culture liquid.

8. The method according to claim 7, wherein the cell size distribution is divided into three portions, firs tone of which is a normal distribution as a living cell region, second one is a homogeneous distribution as a co-presence of living cell and dead cell region, and third one is a dead cell region.

9. A method of diagnosing activity status of the animal cells during culturing the cells, which comprises the steps of:

taking part of a culture liquid containing the animal cells out of a culturing vessel;

taking an optical image of the part of the culture liquid through an optical device;

converting the topical image into electrical signals;

measuring sizes of animal cells in the part of the culture liquid on the basis of the signals by image processing;

calculating a cell size distribution of the animal cells; and diagnosing activity status of the animal cells from the cell size distribution, wherein the same physiological conditions of the taken part of the culture liquid as in the culturing vessel is maintained while the taken part of the culture liquid is out of the culturing vessel.

10. A method of diagnosing activity status of the animal cells during culturing the cells, which comprises the steps of:

taking part of a culture liquid containing the animal cells out of a culturing vessel;

taking an optical image of the part of the culture liquid through an optical device;

converting the topical image into electrical signals;

measuring sizes of animals cells in the part of the culture liquid on the basis of the signals by image processing;

calculating a cell size distribution of the animal cells;

diagnosing activity status of the animal cells from the cell size distribution, wherein the same physiological conditions of the taken part of the culture liquid as in the culturing vessel is maintained while the taken part of the culture liquid is outside of the culturing vessel; and returning the taken part of the culture liquid to the culturing vessel, while keeping the culture liquid from any contaminates from the outside of the culturing system.

11. The method according to claim 10, wherein the cell size distribution is divided into three portions, first one of which is a normal distribution as a living cell region, second one is a homogeneous distribution as a co-presence of living cell and dead cell region, and third one is a dead cell region.

12. An apparatus for culturing animal cells, which comprises:

a culturing vessel for containing a culture liquid containing animal cells and for performing culturing of animal cells therein;

means for feeding a fresh culture medium to the culture liquid in the culturing vessel;

means for taking from the culturing vessel a part of a culture liquid containing the animal cells and for returning the part of culture liquid to the culturing vessel;

means for picking up an optical image of the animal cells in the part of culture liquid taken outside of the culturing vessel and for converting the optical image to electrical signals;

means for processing the electrical signals to obtain cell size distribution;

means for outputting processed information including cell size distribution of the animal cells; and control means provided so that the physiological conditions of the culture liquid outside of the culture vessel are maintained in the same as in the culture liquid in the culture vessel until the culture liquid is returned to the culture vessel.

13. The apparatus according to claim 12, wherein the apparatus is constructed so that the culture liquid is isolated from the atmosphere during the whole period of culturing.

14. An apparatus for culturing animal cells, which comprises:

a culturing vessel for performing culturing of animal cells therein;

means for feeding a fresh culture medium to the culture vessel;

means for taking from the culturing vessel a part of a culture liquid containing the animal cells and returning the part of culture liquid to the culturing vessel, while maintaining physiological conditions the same as in the culture liquid in the culture vessel;

means for picking up an optical image of the animal cells in the part of culture liquid taken outside of the culturing vessel and for converting the optical image to electrical signals;

means for processing the electrical signals to obtain cell size distribution; and means for outputting processed information including cell size distribution of the animal cells.

15. The apparatus according to claim 14, wherein the outputting means displays the cell size distribution comprising three portions, first one of which is a normal distribution as a living cell region, second one is a homogeneous distribution as a co-presence of living cell and dead cell region, and third one is a dead cell region.

16. The apparatus according to claim 14, wherein the apparatus is constructed so the culture liquid is isolated from the atmosphere during the whole period of culturing.

* * * * *